United States Patent
Fan et al.

(10) Patent No.: US 11,084,772 B2
(45) Date of Patent: Aug. 10, 2021

(54) PROCESS FOR CONTINUOUSLY PRODUCING POLYOXYMETHYLENE DIMETHYL ETHERS AT LOW TEMPERATURE

(71) Applicants: Institute of Coal Chemistry, Chinese Academy of Sciences, Taiyuan (CN); Shanxi Lu'an Mining (Group) Co., Ltd., Changzhi (CN)

(72) Inventors: Weibin Fan, Taiyuan (CN); Guofu Wang, Taiyuan (CN); Jiaqi Guo, Taiyuan (CN); Jianguo Wang, Taiyuan (CN); Mei Dong, Taiyuan (CN); Pengfei Wang, Taiyuan (CN); Youliang Cen, Taiyuan (CN); Yaning Xiao, Taiyuan (CN); Dongfei Wang, Taiyuan (CN); Shoujing Sun, Taiyuan (CN); Weilin Wang, Taiyuan (CN); Juncai Zhang, Taiyuan (CN); Min Zhang, Taiyuan (CN); Yunhong Li, Taiyuan (CN)

(73) Assignees: Institute of Coal Chemistry, Chinese Academy of Sciences, Taiyuan (CN); Shanxi Lu'an Mining (Group) Co., Ltd., Changzhi (CN)

( * ) Notice: Subject to any disclaimer, the term of this patent is extended or adjusted under 35 U.S.C. 154(b) by 0 days.

(21) Appl. No.: 16/860,603

(22) Filed: Apr. 28, 2020

(65) Prior Publication Data
US 2020/0339495 A1 Oct. 29, 2020

(30) Foreign Application Priority Data
Apr. 29, 2019 (CN) .......................... 201910356736.5

(51) Int. Cl.
| | |
|---|---|
| C07C 41/56 | (2006.01) |
| B01D 67/00 | (2006.01) |
| B01D 69/04 | (2006.01) |
| B01J 4/00 | (2006.01) |
| B01J 19/00 | (2006.01) |
| B01J 19/18 | (2006.01) |
| B01J 29/40 | (2006.01) |
| B01J 29/70 | (2006.01) |
| C07C 41/58 | (2006.01) |
| B01D 71/02 | (2006.01) |
| C07C 43/303 | (2006.01) |

(52) U.S. Cl.
CPC .......... *C07C 41/56* (2013.01); *B01D 67/0072* (2013.01); *B01D 69/04* (2013.01); *B01J 4/008* (2013.01); *B01J 19/0066* (2013.01); *B01J 19/18* (2013.01); *B01J 29/40* (2013.01); *B01J 29/7007* (2013.01); *B01J 29/7038* (2013.01); *C07C 41/58* (2013.01); *B01D 71/022* (2013.01); *B01D 2325/02* (2013.01); *B01J 2219/00033* (2013.01); *B01J 2219/00051* (2013.01); *B01J 2219/00761* (2013.01); *C07C 43/303* (2013.01)

(58) Field of Classification Search
CPC ...................................................... C07C 41/56
See application file for complete search history.

(56) References Cited

U.S. PATENT DOCUMENTS 9,266,990 B2 * 2/2016 Wang ...................... C07C 41/58

OTHER PUBLICATIONS

Wu et al. High Si/Al ratio HZSM-5 zeolite : an efficient catalyst for the synthesis of polyoxymethylene dimethyl ethers from dimethoxymethane and trioxymethylene. Green Chemistry, vol. 15, 2353-2357. (Year: 2015).*
Wang et al. Synthesis of polyoxymethylene dimethyl ethers from dimethoxymethane and trioxymethylene over graphene oxide: Probing the active species and relating the catalyst structure to performance. Applied Catalysis A, General, vol. 570, 15-22. (Year: 2019).*
Baranowski et al. Prominent role of mesopore surface area and external acid sites for the synthesis of polyoxymethylene dimethyl ethers (OME) on a hierarchical H-ZSM-5 zeolite. Catalysis Science & Technology, vol. 9, 366-376. (Year: 2019).*

* cited by examiner

*Primary Examiner* — Sikarl A Witherspoon
(74) *Attorney, Agent, or Firm* — Andrus Intellectual Property Law, LLP

(57) ABSTRACT

The disclosure relates to a process for continuously producing polyoxymethylene dimethyl ethers at low temperature, pertains to the technical field of polyoxymethylene dimethyl ether preparation processes, and solves the technical problem of continuous production of polyoxymethylene dimethyl ether. A membrane separation element with precisely controlled pores in membrane is used to realize a direct separation of the feedstocks from the catalyst within the reactor, and effectively reduce the permeation resistance of the separation membrane tube. By oppositely switching the flowing direction of liquid reaction materials, the adhesion of the catalyst to the separation membrane tube is inhibited, and some particles stuck in separation membrane tube are removed, which ensures the continuous operation of the reaction process and allows a molecular sieve catalyst to exhibit its advantage of long catalytic life.

7 Claims, 1 Drawing Sheet

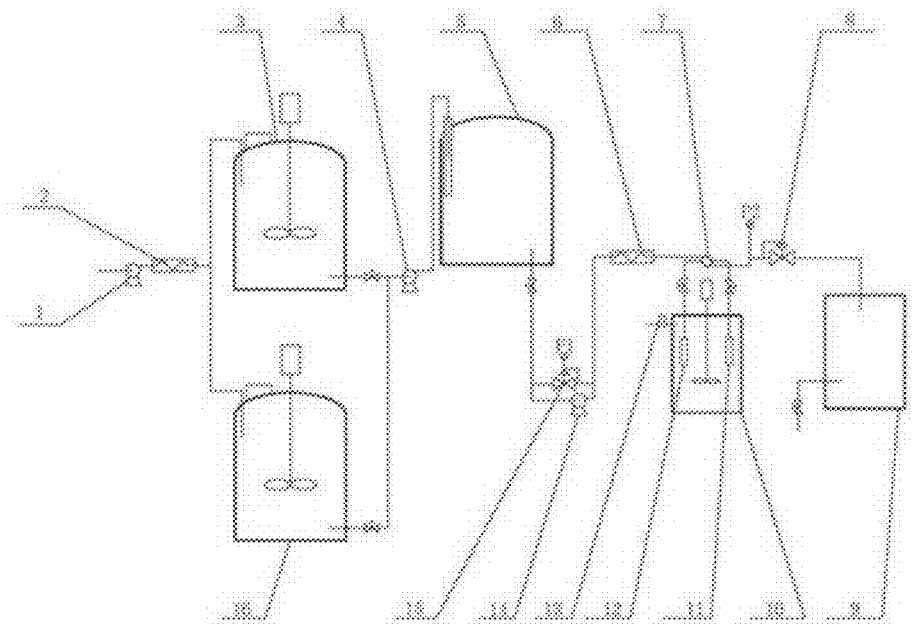

PROCESS FOR CONTINUOUSLY PRODUCING POLYOXYMETHYLENE DIMETHYL ETHERS AT LOW TEMPERATURE

TECHNICAL FIELD

The disclosure pertains to the technical field of polyoxymethylene dimethyl ether preparation processes, and particularly relates to a process for continuously producing polyoxymethylene dimethyl ethers at low temperature.

BACKGROUND

Polyoxymethylene dimethyl ethers ($CH_3$—O—($CH_2$—O)$_n$—$CH_3$, n≥2, abbreviated as $DMM_n$) are a new type of polyether derived from methanol, wherein $DMM_{2-8}$, as diesel additives, can significantly improve the combustion conditions in diesel engines and effectively reduce the emissions of CO, $NO_x$ and particulate pollutants due to the high oxygen content and cetane number thereof. $DMM_{2-8}$ can be synthesized by polymerization of methanol or dimethoxymethane (DMM) with formaldehyde (FA), trioxymethylene (TOM) or polyformaldehyde ($PF_n$). Therefore, the efficient preparation of $DMM_{2-8}$ from methanol and derivatives thereof is of great interest as it not only alleviates the current over-production of methanol, but also develops a new coal chemical technology.

In this context, many researchers have been devoting to the synthesis of $DMM_n$. Patent No. 2016105989527 reports the use of dimethoxymethane (DMM) and trioxymethylene (TOM) or polyformaldehyde (PF) as the reaction materials to synthesize $DMM_n$, where the catalyst is separated from the reaction materials and products by using a membrane separation technology. This technology does not need a separate catalyst separation procedure, thereby achieving a semi-continuous operation of the chemical process. However, in this technology (provided by the patent No. 2016105989527) still exists a serious problem that solid powder adheres to the separation membrane tube in a long run, which affects the continuity of operation and cannot reflect the long catalytic life advantage of catalysts. Therefore, this technology is difficult to be applied and spread in industry.

SUMMARY

The object of the disclosure is: the disclosure provides a process for continuous production of polyoxymethylene dimethyl ether at low temperature in order to solve the technical problem of continuous production of polyoxymethylene dimethyl ether.

The disclosure uses dimethoxymethane (DMM) and trioxymethylene (TOM) as reaction materials to reduce the generation of by-products such as hemiacetal, water and so on. A molecular sieve catalyst with appropriate silicon to aluminum ratio, morphology and particle size is selected to achieve a smooth reaction at low temperature. During this reaction, the low reaction temperature suppresses side reactions and improves product selectivity. The preferred silicon to aluminum ratio provides suitable acidity and numbers of acid sites. Under the premise of keeping the reactant conversion and the product selectivity, the amount of the used dimethoxymethane is further reduced, and the productivity per unit time is increased.

By precisely controlling the pore size of a membrane, direct separation of the feedstocks from the catalyst achieved within the reactor, and simultaneously, the permeation resistance of the separation membrane tube is effectively reduced. The adhesion of the catalyst particles to the separation membrane tube is inhibited, and some catalyst particles are removed by oppositely switching reaction liquid flow direction at designed time interval. It ensures the continuous operation of the reaction process and allows the catalyst to show its long catalytic life advantage.

The present process greatly reduces the cost and energy consumption for synthesis of $DMM_n$, and has broad and potential industrial application prospects.

The disclosure is realized by the following technical solutions.

A process for continuously producing polyoxymethylene dimethyl ether at low temperature, comprising the following steps:

S1. A barrel pump is in communication with a first and a second dispensers respectively through a DMM preheater; the first and the second dispensers are both charged with trioxymethylene; the barrel pump alternately feeds preheated dimethoxymethane into the first dispenser and the second dispenser to form uniform reaction materials; and the uniform reaction materials are pumped into a material tank through a first feed pump; wherein the molar ratio of dimethoxymethane to trioxymethylene is (2-10):1;

S2. A solid catalyst is added in a reactor, and the reaction materials in the material tank are pumped by a second feed pump into the reactor through a four-way channel valve. The two radially opposite ports of the four-way channel valve are respectively connected to the first and the second separation membrane tubes; the other two radially opposite ports of the four-way channel valve are respectively connected to the inlet and the outlet of the reaction materials; the first or the second separation membrane tube alternately feeds or discharges the reaction materials by the channel-switching action of the four-way channel valve; the reaction is carried out in the reactor with the catalyst and the reaction materials being uniformly mixed under a continuous and stable stirring condition; the weight space velocity is controlled at 0.3 to 50 h$^{-1}$; the reaction temperature is maintained at 30 to 69° C.; the reaction pressure is kept at 0.5 to 2.0 MPa;

S3. A gas flow control meter is configured on the upper portion of the reactor side wall; the flow control meter detects and controls the input speed of nitrogen for matching the discharge rate with the feed rate of the reaction materials and controlling the distance of 5-80 cm between the liquid level of the reaction materials and the upper cap through adjustment of the pressure in the reactors; the reaction materials are separated from the catalyst through the first separation membrane tube or the second separation membrane tube at the outlet of the reactor; the catalyst remains in the reactor, while the reaction materials are introduced into a product collection tank;

S4. The mixture in the product collection tank is sent to a subsequent separation device for further separation into product DMM$_{2-8}$ and unreacted materials that are circulated to the material tank.

Further, in step S1, the preheating temperature of dimethoxymethane is 40-32° C., and the preheating temperature of dimethoxymethane decreases as the molar ratio of dimethoxymethane to trioxymethylene increases.

Further, in step S2, the second feed pump is connected in parallel with a feed backpressure valve.

Further, in step S2, a reaction preheater is configured on the pipeline connecting the second feed pump and the reactor, and a reaction backpressure valve is configured in the pipeline connecting the four-way channel valve and the product collection tank.

Further, the reactor is a stainless steel reactor and is equipped with a continuous stirring device.

Further, the solid catalyst is selected to be a ZSM-5 molecular sieve, a MCM-22 molecular sieve or an Hβ molecular sieve.

Further, the first separation membrane tube and the second separation membrane tube are made from powder metallurgy stainless steel membrane tube with pore size controlled by chemical vapor deposition.

Compared with the prior art, the beneficial effects of the disclosure include:

(1) The catalyst can achieve a long-term continuous operation while having a good mechanical strength;

(2) The process is simple, and the reaction conditions are mild;

(3) The product selectivity is high.

BRIEF DESCRIPTION OF THE DRAWINGS

FIG. 1 is a schematic diagram of the overall structure of the disclosure;

In the FIGURE, 1 is a barrel pump, 2 is a DMM preheater, 3 is a first dispenser, 4 is a first feed pump, 5 is a material tank, 6 is a reaction preheater, 7 is a four-way channel valve, 8 is a reaction backpressure valve, 9 is a product collection tank, 10 is a reactor, 11 is a first separation membrane tube, 12 is a second separation membrane tube, 13 is a flow control meter, 14 is a second feed pump, 15 is a feed backpressure valve, and 16 is a second dispenser.

DESCRIPTION OF THE EMBODIMENTS

The disclosure is further described in detail with reference to the drawing FIGURE and examples.

A process for continuously producing polyoxymethylene dimethyl ether at low temperature, as shown in FIG. 1, comprises the following steps:

S1. A barrel pump 1 is in communication with a first dispenser 3 and a second dispenser 16 respectively through a DMM preheater 2; the first dispenser 3 and the second dispenser 16 are both charged with trioxymethylene; the barrel pump 1 alternately feeds preheated dimethoxymethane into the first dispenser 3 and the second dispenser 16 to form uniformly mixed materials; and the uniformly mixed materials are pumped into a material tank 5 through a first feed pump 4; wherein the molar ratio of dimethoxymethane to trioxymethylene is (2-10):1;

S2. A solid catalyst is added in a reactor 10, and the reaction materials in the material tank 5 are pumped by a second feed pump 14 into the reactor through a four-way channel valve 7. The two radially opposite ports of the four-way channel valve 7 are respectively connected to the first separation membrane tube 11 and the second separation membrane tube 12; the other two radially opposite ports of the four-way channel valve are respectively connected to the inlet and the outlet of the reaction materials; the first separation membrane tube 11 or the second separation membrane tube 12 alternately feeds or discharges the reaction materials by the channel-switching action of the four-way channel valve; the reaction is carried out in the reactor 10 with the catalyst and the reaction materials being uniformly mixed by a continuous and stable stirring; the mass space velocity is controlled at 0.3 to 50 h$^{-1}$; the reaction temperature is kept at 30 to 69° C.; and the reaction pressure is maintained at 0.5 to 2.0 MPa;

S3. A gas flow control meter 13 is configured on the upper portion of the side wall of the reactor 10; the flow control meter 13 detects and controls the input speed of nitrogen for matching the discharge rate with the feed rate of the reaction materials, and controlling the distance between the liquid level of the reaction materials and the upper cap of the reactor 10 to be 5-80 cm through adjustment of the pressure in the reactor; the reaction materials are separated from the catalyst through the first separation membrane tube 11 or the second separation membrane tube 12 at the outlet of the reactor 10; the catalyst remains in the reactor 10, while the reaction materials are introduced into a product collection tank 9;

S4. The mixture in the product collection tank 9 is sent to a subsequent separation device for further separation into product DMM$_{2-8}$ and unreacted materials that are circulated to the material tank 5.

Further, in step S1, the preheating temperature of dimethoxymethane is 40-32° C., and it decreases as the molar ratio of dimethoxymethane to trioxymethylene increases.

Further, in step S2, the second feed pump 14 is connected in parallel with a feed backpressure valve 15.

Further, in step S2, a reaction preheater 6 is configured in the pipeline connecting the second feed pump 14 and the reactor 10, and a reaction backpressure valve 8 is installed in the pipeline connecting the four-way channel valve and the product collection tank 9.

Further, the reactor 10 is a stainless steel reactor and is equipped with a continuous stirring device.

Further, the solid catalyst is selected to be a ZSM-5 molecular sieve, a MCM-22 molecular sieve or an Hβ molecular sieve.

Further, the first separation membrane tube 11 and the second separation membrane tube 12 are made of powder metallurgy stainless steel membrane tube with pore size adjusted by chemical vapor deposition.

The disclosure is described in detail by the following examples:

Example 1

The reactor 10 with an effective capacity of 500 mL is charged with 20 g of MCM-22 molecular sieve catalyst having a high silica to aluminum ratio. The dimethoxymethane preheated to 40° C. is fed into the first dispenser 3 (or the second dispenser 16) already charged with trioxymethylene, and uniformly mixed, wherein the molar ratio of dimethoxymethane to trioxymethylene is 2:1. The uniformly mixed materials are continuously pumped by the second feed pump 14 into the reactor 10 with the catalyst and the reaction materials being uniformly mixed through a continuous and stable stirring. During the reaction, the temperature of the reactor is controlled at 40° C.; the flow rate of the second feed pump 14 is 5 mL/min; the time interval for regularly switching the four-way channel valve 7 is 6 hours; the opening pressure of the reaction backpressure valve 8 is 0.5 MPa; the opening pressure of the feed backpressure valve 15 is 1.3 MPa. The initial pressure of the gas flow control meter 13 is 5 sccm, and then, adjusted according to the changes of the liquid level, i.e., the flow rate of the gas flow control meter 13 is increased as the liquid level rises, and is reduced as the liquid level declines.

The operation is stable for more than 800 consecutive hours. The material conversion is reduced slightly in the later period, but the product selectivity remains high. The specific results are as follows:

| Time(h) | 5 | 107 | 202 | 514 | 634 | 682 | 730 | 751 | 798 | 820 |
|---|---|---|---|---|---|---|---|---|---|---|
| DMM Conv. (%) | 47.9 | 50.3 | 51.7 | 53.3 | 52.4 | 50.3 | 50.3 | 48.0 | 45.6 | 44.5 |
| TOM Conv. (%) | 94.9 | 95.2 | 94.7 | 92.1 | 91.7 | 90.8 | 86.1 | 84.4 | 82.2 | 82.6 |
| $DMM_{2-8}$ Sel. (%) | 93.1 | 92.0 | 95.3 | 95.3 | 94.3 | 95.2 | 94.4 | 94.3 | 94.3 | 94.5 |

Example 2

The reactor 10 with an effective capacity of 500 mL is charged with 20 g of ZSM-5 molecular sieve catalyst having a low silica to aluminum ratio. The dimethoxymethane preheated to 35° C. is fed into the first dispenser 3 (or the second dispenser 16) charged with trioxymethylene, and uniformly mixed, wherein the molar ratio of dimethoxymethane to trioxymethylene is 6:1. The mixed materials are continuously pumped by the second feed pump 14 into the reactor 10, and the reaction is carried out with the catalyst and the reaction materials being uniformly mixed under continuously and stably stirring conditions. During the reaction, the temperature of the reactor is controlled at 60° C.; the flow rate of the second feed pump 14 is 10 mL/min; the time interval of regularly switching the four-way channel valve 7 is 6 hours; the opening pressure of the reaction backpressure valve 8 is 0.6 MPa; the opening pressure of the feed backpressure valve 15 is 1.5 MPa. The initial pressure of the gas flow control meter 13 is 5 sccm, and then, adjusted according to the changes of the liquid level, i.e., the flow rate of the gas flow control meter 13 is increased as the liquid level rises, and the flow rate of the gas flow control meter 13 is decreased as the liquid level declines.

The operation is consecutively stable for more than 500 hours. The reactant conversion is slightly decreased in the later period, but the product selectivity remains high. The specific results are as follows:

| Time(h) | 5 | 120 | 228 | 310 | 407 | 456 | 486 | 491 | 515 | 563 |
|---|---|---|---|---|---|---|---|---|---|---|
| DMM Conv. (%) | 49.7 | 51.3 | 51.1 | 51.9 | 52.6 | 50.8 | 50.4 | 49.7 | 49.5 | 47.1 |
| TOM Conv. (%) | 89.6 | 92.5 | 93.6 | 92.2 | 92.2 | 92.5 | 92.7 | 92.7 | 92.5 | 84.0 |
| $DMM_{2-8}$ Sel. (%) | 93.6 | 93.6 | 93.7 | 93.2 | 93.8 | 93.4 | 93.5 | 93.6 | 93.5 | 93.5 |

Example 3

The reactor 10 with an effective volume of 500 mL is charged with 20 g of Hβ molecular sieve catalyst. The dimethoxymethane preheated to 32° C. is fed into the first dispenser 3 (or the second dispenser 16) already charged with trioxymethylene, and uniformly mixed, wherein the molar ratio of dimethoxymethane to trioxymethylene is 10:1. The mixed materials are continuously sent by the second feed pump 14 into the reactor 10, and the reaction is carried out with the catalyst and the reaction materials being uniformly mixed under a continuous and stable stirring condition. During the reaction, the temperature of the reactor is controlled at 69° C.; the flow rate of the second feed pump 14 is 10 mL/min; the time interval of regularly switching the four-way channel valve 7 is 6 hours; the opening pressure of the reaction backpressure valve 8 is 0.6 MPa; the opening pressure of the feed backpressure valve 15 is 1.5 MPa. The initial pressure of the gas flow control meter 13 is 5 sccm, and then, adjusted according to the changes of the liquid level, i.e., the flow rate of the gas flow control meter 13 is elevated as the liquid level rises, and the flow rate of the gas flow control meter 13 is lowered down as the liquid level declines.

Confirmatory operation is continuously run for about 100 hours. Both the reactant conversion and the product selectivity remains unchanged. The specific results are as follows:

| Time(h) | 3 | 9 | 20 | 30 | 40 | 50 | 62 | 74 | 86 | 98 |
|---|---|---|---|---|---|---|---|---|---|---|
| DMM Conv. (%) | 19.4 | 50.7 | 50.2 | 51.3 | 5.6 | 51.5 | 50.9 | 51.7 | 51.8 | 50.7 |
| TOM Conv. (%) | 41.1 | 91.6 | 92.8 | 92.0 | 92.7 | 92.8 | 91.9 | 91.0 | 91.6 | 91.8 |
| $DMM_{2-8}$ Sel. (%) | 83.5 | 91.2 | 91.1 | 91.2 | 91.9 | 92.4 | 92.4 | 91.8 | 91.2 | 91.1 |

Example 4

The reactor 10 with an effective capacity of 500 mL is charged with 20 g of MCM-22 molecular sieve catalyst having a silica to aluminum ratio of 50. The dimethoxymethane preheated to 40° C. is sent into the first dispenser 3 (or the second dispenser 16) already charged with trioxymethylene, and uniformly mixed, wherein the molar ratio of dimethoxymethane to trioxymethylene is 2.5:1. The mixed materials are continuously pumped by the second feed pump 14 into the reactor 10, and the reaction is carried out with the conditions that the catalyst and the reaction materials being uniformly mixed under a continuous and stable stirring condition. During the reaction, the temperature of the reactor is controlled at 35° C.; the flow rate of the second feed pump 14 is 1 mL/min; the time interval of regularly switching the four-way channel valve 7 is 8 hours; the opening pressure of the reaction backpressure valve 8 is 0.4 MPa; the opening pressure of the feed backpressure valve 15 is 1.5 MPa. The initial pressure of the gas flow control meter 13 is 5 sccm, and then, adjusted in terms of the changes of the liquid level, i.e., the flow rate of the gas flow control meter 13 is elevated as the liquid level rises, and the flow rate of the gas flow control meter 13 is reduced as the liquid level declines.

Confirmatory operation is continuously run for about 100 hours. Both the material conversion is slightly lower, but the product selectivity remains unchanged. The specific results are as follows:

| Time(h) | 4 | 10 | 21 | 33 | 45 | 57 | 69 | 81 | 93 | 105 |
|---|---|---|---|---|---|---|---|---|---|---|
| DMM Conv. (%) | 19.4 | 50.7 | 50.2 | 50.3 | 50.6 | 50.5 | 50.9 | 50.7 | 50.8 | 50.7 |
| TOM Conv. (%) | 41.1 | 92.6 | 92.3 | 93.1 | 92.5 | 91.8 | 91.9 | 92.0 | 91.6 | 91.8 |
| $DMM_{2-8}$ Sel. (%) | 83.5 | 96.2 | 97.1 | 97.2 | 97.9 | 98.2 | 98.1 | 97.8 | 97.2 | 97.3 |

The above examples are only specific embodiments of this disclosure, but the protection scope of the disclosure is not limited thereto. Any variations or substitutions that can be easily conceived by those skilled in the art within the technical scope disclosed by this disclosure shall be included in the protection scope of this disclosure. Therefore, the protection scope of this disclosure shall be subject to the protection scope of the claims.

The invention claimed is:

1. A process for continuously producing polyoxymethylene dimethyl ether at low temperature, characterized by comprising the following steps:
    S1. A barrel pump (1) is in communication with a first dispenser (3) and a second dispenser (16) respectively through a DMM preheater (2); the first dispenser (3) and the second dispenser (16) are both charged with trioxymethylene; the barrel pump (1) alternately pumps preheated dimethoxymethane into the first dispenser (3) or the second dispenser (16) to form uniform mixture; and the uniform mixture is pumped into a material tank (5) through a first feed pump (4); wherein the molar ratio of dimethoxymethane to trioxymethylene is (2-10):1;
    S2. A solid catalyst is added in a reactor (10), and the reaction materials in the material tank (5) are pumped by a second feed pump (14) into the reactor through a four-way channel valve (7); The two radially opposite ports of the four-way channel valve (7) are respectively connected to the first separation membrane tube (11) and the second separation membrane tube (12); and the other two radially opposite ports of the four-way channel valve are respectively connected to the inlet and the outlet of the reaction materials; the first separation membrane tube (11) or the second separation membrane tube (12) alternately feeds or discharges the reaction materials by the channel-switching action of the four-way channel valve; the reaction is carried out in the reactor (10) with the catalyst and the reaction materials being uniformly mixed under a continuous and stable stirring condition; the weight space velocity is controlled at 0.3 to 50 $h^{-1}$; the reaction temperature is 30 to 69° C.; the reaction pressure is 0.5 to 2.0 MPa;
    S3. A gas flow control meter (13) is configured on the upper part of the side wall of the reactor (10); the flow control meter (13) detects and controls the input speed of nitrogen for matching the discharge rate with the feed rate of the reaction materials and controlling the distance between the liquid level of the reaction materials and the upper cap of the reactor (10) to be 5 to 80 cm by adjusting the pressure in the reactor; the reaction materials are separated from the catalyst through the first separation film tube (11) or the second separation film tube (12) at the outlet of the reactor (10); the catalyst remains in the reactor (10), while the reaction materials are introduced into a product collection tank (9);

S4. The mixture in the product collection tank (9) is sent to a subsequent separation device for further separation into reaction product $DMM_{2-8}$ and unreacted materials; the unreacted materials are circulated to the material tank (5).

2. The process for continuously producing polyoxymethylene dimethyl ether at low temperature according to claim 1, characterized by that in step S1, the preheating temperature of dimethoxymethane is 40 to 32° C., and the preheating temperature of dimethoxymethane decreases as the molar ratio of dimethoxymethane to trioxymethylene increases.

3. The process for continuously producing polyoxymethylene dimethyl ether at low temperature according to claim 1, characterized by that in step S2, the second feed pump (14) is connected in parallel with a feed backpressure valve (15).

4. The process for continuously producing polyoxymethylene dimethyl ether at low temperature according to claim 1, characterized by that in step S2, a reaction preheater (6) is configured in the pipeline connecting the second feed pump (14) and the reactor (10), and a reaction backpressure valve (8) is installed in the pipeline connecting the four-way channel valve and the product collection tank (9).

5. The process for continuously producing polyoxymethylene dimethyl ether at low temperature according to claim 1, characterized by that the reactor (10) is a stainless steel reactor and is equipped with a continuous stirring device.

6. The process for continuously producing polyoxymethylene dimethyl ether at low temperature according to claim 1, characterized by that the solid catalyst is selected to be a ZSM-5 molecular sieve, a MCM-22 molecular sieve or an Hβ molecular sieve.

7. The process for continuously producing polyoxymethylene dimethyl ether at low temperature according to claim 1, characterized by that the first separation membrane tube (11) and the second separation membrane tube (12) are made of a powder metallurgy stainless steel membrane tube with pore size adjusted by chemical vapor deposition.

\* \* \* \* \*